United States Patent
Klein et al.

(10) Patent No.: US 9,289,421 B2
(45) Date of Patent: Mar. 22, 2016

(54) METHODS AND COMPOSITIONS FOR REDUCING SERUM LEVELS OF IMMUNOGLOBULIN E (IGE)

(75) Inventors: Thomas W. Klein, Tampa, FL (US); Catherine Newton, Land of Lakes, FL (US); Catherine Patterson, Lutz, FL (US); Marisela Agudelo, Miami, FL (US)

(73) Assignee: UNIVERSITY OF SOUTH FLORIDA FL (US)

( * ) Notice: Subject to any disclaimer, the term of this patent is extended or adjusted under 35 U.S.C. 154(b) by 158 days.

(21) Appl. No.: 14/241,388

(22) PCT Filed: Aug. 29, 2012

(86) PCT No.: PCT/US2012/052787
§ 371 (c)(1),
(2), (4) Date: Jul. 14, 2014

(87) PCT Pub. No.: WO2013/033155
PCT Pub. Date: Mar. 7, 2013

(65) Prior Publication Data
US 2014/0350052 A1    Nov. 27, 2014

Related U.S. Application Data

(60) Provisional application No. 61/530,097, filed on Sep. 1, 2011, provisional application No. 61/542,471, filed on Oct. 3, 2011.

(51) Int. Cl.
*A61K 31/454* (2006.01)
*A61K 31/416* (2006.01)
*A61K 31/496* (2006.01)

(52) U.S. Cl.
CPC ............. *A61K 31/454* (2013.01); *A61K 31/416* (2013.01); *A61K 31/496* (2013.01)

(58) Field of Classification Search
CPC .................................................. A61K 31/454
USPC ....................................................... 514/322
See application file for complete search history.

(56) References Cited

U.S. PATENT DOCUMENTS

| | | | |
|---|---|---|---|
| 2010/0197755 A1 | 8/2010 | Attala et al. | |
| 2010/0215741 A1 | 8/2010 | Lazzari et al. | |
| 2010/0216785 A1 | 8/2010 | Lazzari et al. | |
| 2011/0092567 A1 | 4/2011 | Klein et al. | |

OTHER PUBLICATIONS

Baker et al., (2006) In silico patent searching reveals a new cannabinoid receptor. Trends Pharmacol. Sci. 27: 1-4.
Begg et al., (2005) Evidence for novel cannabinoid receptors. Pharmacol. Ther. 106: 133-145.
Bouaboula et al., (1999) Regulation of Peripheral Cannabinoid Receptor CB 2Phosphorylation by the Inverse Agonist SR 144528: Implications for Receptor Biological Responses. J. Biol. Chem. 274: 20397-20405.
Howlett et al., (2002) Classification of Cannabinoid Receptors. Pharmacol. Rev. 54: 161-202.
Jbilo et al., (1999) Stimulation of peripheral cannabinoid receptor CB2 induces MCP-1 and IL-8 gene expression in human promyelocytic cell line HL60. FEBS Lett. 448: 273-277.
Kaplan et al., (2010) The Effects of Targeted Deletion of Cannabinoid Receptors CB1 and CB2 on Intranasal Sensitization and Challenge with Adjuvant-free Ovalbumin. Toxicol. Pathol. 38: 382-392.
Kishimoto et al., (2004) 2-Arachidonoylglycerol, an Endogenous Cannabinoid Receptor Ligand, Induces Accelerated Production of Chemokines in HL-60 Cells. J. Biochem. 135:15 517-524.
Klein et al., (2000) Delta 9-Tetrahydrocannabinol Treatment Suppresses Immunity and Early IFN-gamma, IL-12, and IL-12 Receptor Beta2 Responses to Legionella pneumophila Infection. J. Immunol. 164: 6461-6466.
Klein TW (2005) Cannabinoid-Based Drugs as Anti-Inflammatory Therapeutics. Nat. Rev. Immunol. 5: 400-411.
Lauckner et al., (2008) GPR55 is a cannabinoid receptor that increases intracellular calcium and inhibits M current. Proc. Natl. Acad. Sci. U.S.A 105:2699-2704.
Lu et al., (2006) Role of cannabinoid receptors in Delta-9-tetrahydrocannabinol suppression of IL-12p40 in mouse bone marrow-derived dendritic cells infected with Legionella pneumophila Eur. J. Pharmacol. 532: 170-177.
Maresz et al., (2007) Direct suppression of CNS autoimmune inflammation via the cannabinoid receptor CB1 on neurons and CB2 on autoreactive T cells. Nat. Med. 13:492-497.
Mussinu et al., (2003) Tricyclic Pyrazoles. Part 1: Synthesis and Biological Evaluation of Novel 1,4-Dihydroindeno[1,2- c]pyrazol-based Ligands for CB1 and CB2 Cannabinoid Receptors. Bioorganic Medicinal Chem. 11: 251-263.
Newton et al., (1994) Secondary immunity to Legionella pneumophila and Th1 activity are suppressed by delta-9-tetrahydrocannabinol injection. Infect. Immun. 62: 4015-4020.
Newton et al., (2009) CB1 and CB2 Cannabinoid Receptors Mediate Different Aspects of Delta-9-Tetrahydrocannabinol (THC)-Induced T Helper Cell Shift Following Immune Activation by Legionella Pneumophila Infection. J. Neuroimmune Pharmacol. 4: 92-102.
Oka et al., (2007) Identification of GPR55 as a lysophosphatidylinositol receptor. Biochem. Biophys. Res. Commun. 362: 928-934.
Oka et al., (2009) 2-Arachidonoyl-sn-glycero-3-phosphoinositol: A Possible Natural Ligand for GPR55J. Biochem. 145: 13-20.
Pertwee RG (1997) Pharmacology of Cannabinoid CB1 and CB2 Receptors. Pharmacol. Ther. 74: 129-180.
Pertwee, R. G. (2006) Cannabinoid pharmacology: the first 66 years. Br. J. Pharmacol. 147(Suppl 1): S163-S171.

(Continued)

*Primary Examiner* — Raymond Henley, III
(74) *Attorney, Agent, or Firm* — Thomas|Horstemeyer, LLP

(57) ABSTRACT

The present disclosure provides methods and pharmaceutical compositions for reducing the serum level of immunoglobulin IgE in an animal or human subject. It has been found that reducing or inhibiting the activity of the cannabinoid receptor CB2 leads to an increase in IgE in serum levels. Conversely, activation of the CB2 receptor by an agonist results in a reduction in IgE serum levels. The compositions and methods of the disclosure, therefore, provide a means to reduce or eliminate symptoms of immune system-related conditions resulting from IgE generation, such as an allergy, hay fever, and the like.

5 Claims, 6 Drawing Sheets

(56) References Cited

OTHER PUBLICATIONS

Pertwee, R. G. (2006) The pharmacology of cannabinoid receptors and their ligands: an overview. Int. J. Obes. 30 (Suppl 1): S13-S18.

Rachelefsky et al., (1976) Intact humoral and cell-mediated immunity in chronic marijuana smoking. Gary S.J. Allergy Clin. Immunol. 58: 483-490.

Roper et al., (1990) Prostaglandin E2 Promotes IL-4-Induced IgE and IgG1 Synthesis. J. Immunol. 145: 2644-2651.

Roy et al., (2001) Morphine directs T cells toward TH2 differentiation. Surgery 130: 304-309.

Ryberg et al., (2007) The orphan receptor GPR55 is a novel cannabinoid receptor. Br. J. Pharmacol. 152: 1092-1101.

Springs et al., (2008) Effects of targeted deletion of cannabinoid receptors CB1 and CB2 on immune competence and sensitivity to immune modulation by Delta9-tetrahydrocannabinol J. Leukoc. Biol. 84: 1574-1584.

Ueda et al., (2007) Involvement of cannabinoid CB2 receptors in the IgE-mediated triphasic cutaneous reaction in mice. Life Sci. 80: 414-419.

Walter & Stella (2004) Cannabinoids and neuroinflammation. Br. J. Pharmacol. 141: 775-785.

Murineddu, G., et al. Tricyclic pyrazoles. 4. Synthesis and biological evaluation of analogues of the robust and selective CB2 cannabinoid ligand 1-(2', 4'-dichlorophenyl)-6-methyl1-N-peperidin-1-yl-1, 4-dihydroindeno{1,2-c}pyrazole-3-carboxamide J. Med. Chem., 2006, vol. 49, Issue 25, pp. 7502-7512. See abstract; p. 7505, right-column; p. 7506, left-column; table 1; and figure 1.

Murineddu, G., et al. 'Tricyclic pyrazoles, Part 2: Synthesis and biological evaluation of novel 4, 5-dihydro-1H-benzo{g}indazole-based ligands for cannabinoid receptors.' Bioorganic & Medicinal Chemistry, 2005, vol. 13, Issue 9, pp. 3309-3320. See abstract; p. 3311, right-column; table 1; and figure 2.

International Search Report and Written Opinion, mailed Jan. 29, 2013.

International Search Report mailed Jan. 29, 2013 for PCT/US2012/052787.

Murineddu et al. Tricyclic Pyrazoles. 4. Synthesis and Biological Evaluation of Analogues of the Robust and Selective CB2 Cannabinoid Ligand 1-(2',4'-Dichlorophenyl)-6-methyl-N-piperidin-1-yl-1,4-dihydroindeno[1,2-c]pyrazole-3-carboxamide. J. Med. Chem., 2006, 49 (25), pp. 7502-7512.

Murineddu et al. Tricyclic pyrazoles. Part 2: Synthesis and biological evaluation of novel 4,5-dihydro-1H-benzo[g]indazole-based ligands for cannabinoid receptors. Bioorganic & Medicinal Chemistry. vol. 13, Issue 9, May 2, 2005, pp. 3309-3320.

Newton & Klein. Cannabinoid 2 (CB2) Receptor Involvement in the Down-regulation but not Up-regulation of Serum IgE Levels in Immunized Mice. J Neuroimmune Pharmacol (2012) 7:591-598.

| Compound | R | R1 | Q |
|---|---|---|---|
| a | 6Cl | 2',4'Cl$_2$ |  |
| b | 6F | 2',4'Cl$_2$ |  |
| c | 6Br | 2',4'Cl$_2$ |  |
| d | 6I | 2',4'Cl$_2$ |  |
| e | 5Cl | 2',4'Cl$_2$ |  |
| f | 7Cl | 2',4'Cl$_2$ |  |
| g | H | 2',4'Cl$_2$ |  |
| h | 6CH$_3$ | 2',4'Cl$_2$ |  |
| i | 6OCH$_3$ | 2',4'Cl$_2$ |  |
| j | 6Cl | 4'Cl$_2$ |  |
| k | 6Cl | H |  |
| l | 6Cl | 4'OCH$_3$ |  |
| m | 6Cl | 2',4'Cl$_2$ |  |
| n | 6Cl | 2',4'Cl$_2$ | -N(CH$_3$)$_2$ |
| o | 6Cl | 2',4'Cl$_2$ | -NH$_2$ |
| p | 6Cl | 2',4'Cl$_2$ |  |
| q | 6Cl | 2',4'Cl$_2$ |  |
| r | 6Cl | 2',4'Cl$_2$ |  |

| Compound | R' | R" | Q |
|---|---|---|---|
| a | CH₃ | H | |
| b | CH₃ | H |  |
| c | CH₃ | H |  |
| d | CH₃ | H |  |
| e | CH₃ | H |  |
| f | CH₃ | H |  |
| g | CH₃ | H |  |
| h | CH₃ | H |  |
| i | CH₃ | H |  |
| j | CH₃ | H |  |
| k | CH₃ | H |  |
| l | CH₃ | H |  |
| m | CH₃ | H |  |
| n | CH₃ | Cl |  |
| o | CH₃ | Cl |  |
| p | Cl | CH₃ |  |
| | | |  |

METHODS AND COMPOSITIONS FOR REDUCING SERUM LEVELS OF IMMUNOGLOBULIN E (IGE)

CROSS-REFERENCE TO RELATED APPLICATION

This application is the 35 U.S.C. §371 national stage of, and claims priority to and the benefit of, PCT application PCT/US2012/052787, filed Aug. 29, 2012, which claims priority to and the benefit of U.S. Provisional Application No. 61/530,097, filed on Sep. 1, 2011, and claims priority to and the benefit of U.S. Provisional Application No. 61/542,471, filed on Oct. 3, 2011 herein incorporated by reference in their entirety.

STATEMENT ON FUNDING PROVIDED BY THE U.S. GOVERNMENT

This invention was made with government support under Grant # R01 DA019824 awarded by National Institutes of Health. The government has certain rights in the invention.

TECHNICAL FIELD

The present disclosure is generally related to pharmaceutical compositions and methods of use thereof for the reduction in the serum level of immunoglobulin E (IgE) in a recipient animal or human subject.

BACKGROUND

Marijuana cannabinoids have been shown to modulate various immune functions through mechanisms involving cannabinoid 1 (CB1) and cannabinoid 1 (CB2) receptors. Several studies have also concluded that other receptors are in involved (Begg et al., (2005) *Pharmacol. Ther.* 106: 133-145) because immune modulation by THC persists in CB1- and CB2-deficient mice (Walter & Stella (2004) *Br. J. Pharmacol.* 141: 775-785; Lu et al., (2006) *Eur. J. Pharmacol.* 532: 170-177; Springs et al., (2008) *J. Leukoc. Biol.* 84: 1574-1584). A third cannabinoid receptor. GPR55, has been reported and may account for some of the effects observed in the relative absence of CB1 and CB2, GPR55 is stimulated by THC as well as other cannabinoid ligands (Ryberg et al., (2007) *Br. J. Pharmacol.* 152: 1092-1101) with one of these ligands, lyso-phosphatidylinositol (LPI), speculated to be the natural endogenous ligand for this receptor (Oka et al., (2009) *J. Biochem.* 145: 13-20).

Among the various immune mechanisms modulated by cannabinoids, T helper (Th) cell biasing has been reported with a suppression of Th1 and enhancement of Th2 immunity (Klein T W (2005) *Nat. Rev. Immunol.* 5; 400-411). This biasing effect of Th cells has also been observed with other neuroimmune agents such as morphine (Roy et al., (2001) *Surgery* 130: 304-309) and could partially explain the decrease in neuroinflammatory symptoms associated with Th1 activity (Maresz et al., (2007) *Nat. Med,* 13:492-497) or the increase in serum IgE levels (Th2 activity) observed in marijuana smokers (Rachelefsky et al., (1976) *J. Allergy Clin. Immunol.* 58: 483-490). In the first report of cannabinoid-induced Th biasing, a suppression of cell-mediated immunity and splenocyte IFN-γ production was accompanied by increasing serum levels of IgG1 antibodies and splenocyte IL-4 (Newton et al., (1994) *Infect. Immun.* 62: 4015-4020). Because the different subclasses of antibodies are regulated by Th cytokines with IL-4 increasing the synthesis of IgG1 and IgE (Roper et al., (1990) *J. Immunol.* 145: 2644-2651), these results suggested that THC might increase the production of the allergic antibody, IgE, in addition to IgG1.

Although it has been shown that CB2 receptors are expressed in peripheral tissues, including, but not limited to tonsils, thymus and spleen, and identified in cells of the central nervous system, it has also been shown that the CB2 receptor is expressed in inflammatory cells and immune competent cells (Howlett et al., (2002) *Pharmacol. Rev.* 54: 161-202; Bouaboula et al., (1999) *J. Biol. Chem.* 274: 20397-20405; Pertwee, R. G. (2006) *Int. J. Obes.* 30 (Suppl 1): S13-S18; Pertwee, R. G. (2006) *Br. J. Pharmacol.* 147 (Suppl 1): S163-S171; Jbilo et al., (1999) *FEBS Lett.* 448: 273-277; Kishimoto et al., (2004) *J. Biochem.* 135: 517-524).

Studies examining the effect of synthetic cannabinoid agonist JWH-015 on CB2 receptors revealed that changes in cAMP levels resulted in the phosphorylation of leukocyte receptor tyrosine kinase at Tyr-505. Through this mechanism, T cell receptor signaling was inhibited. These results further demonstrated the immunosuppressive properties of CB2 receptor agonists. Thus, CB2 agonists have been considered as possibly useful for treatment of inflammation and pain.

SUMMARY

One aspect of the present application, therefore, encompasses embodiments of a method of reducing the serum level of immunoglobulin E (IgE) of an animal or human subject, the method comprising administering to an animal or human subject an effective dose of a pharmaceutical composition comprising an agonist of a CB2 cannabinoid receptor, thereby reducing the serum level of IgE in the serum of the recipient subject.

In embodiments of this aspect of the disclosure, the pharmaceutical composition can further comprise a pharmaceutically acceptable carrier.

In some embodiments of this aspect of the disclosure, the agonist of the CB2 cannabinoid receptor can be 1-(2',4'-Dichlorophenyl)-6-methyl-N-piperidin-1-yl-1,4-dihydroindeno[1,2-c]pyrazole-3-carboxamide (1h).

Another aspect of the disclosure encompasses embodiments of pharmaceutical composition comprising an effective dose of an agonist of a CB2 cannabinoid receptor and a pharmaceutically acceptable carrier, wherein the pharmaceutical composition is formulated to reducing the level of IgE in the serum of the subject animal or human when administered thereto.

BRIEF DESCRIPTION OF THE DRAWINGS

Further aspects of the present disclosure will be more readily appreciated upon review of the detailed description of its various embodiments, described below, when taken in conjunction with the accompanying drawings.

CB1 antagonist) pretreatment of CB2$^{-/-}$ had little effect on total IgE levels. The mice were treated OVA/ALUM following a boost of same antigen. The sera were collected at Day 5-6 after the boost and ELISAs were performed. Data represent serum from individual mice (4-9 mice/group+/−SEM). *=p≤0.05 from Normal; #=p≤0.05 from OVA/ALUM; ##=p<0.05 from THC/OVA/ALUM

Figure 1A:
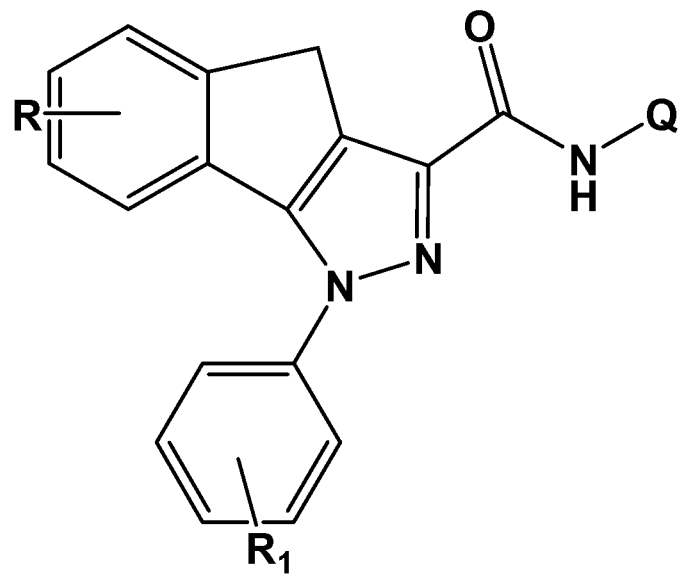
FIG. 1A illustrates the 1,4-dihydroindeno(1,2)pirazole structure of formula 1, derivatives of which are illustrated in FIG. 2.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Definitions

The terms "administration of" and or "administering a" compound should be understood to mean providing a compound of the disclosure or a prodrug of a compound of the disclosure to the individual in need of treatment. The compounds of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "allergy" as used herein refers to an "abnormal hypersensitivity to a substance which is normally tolerated and generally considered harmless. The symptoms of allergies can range from a runny nose to anaphylactic shock. There are two basic phases involved with the allergic response. The first stage involves the development of the early phase of an immediate-type hypersensitivity response to allergens. The first time an allergen meets the immune system, no allergic reaction occurs. Macrophages surround and break up the invading allergen and then display the allergen fragments on their cell walls to T lymphocytes This cognitive signal plus other non-cognitive signals (e.g. cytokines) activate T-cells and instruct their differentiation into T-cell effector subpopulations. Th2 type T-cells can secrete cytokines including interleukin-4 (IL-4), IL-5 and IL-13 that can then activate B lymphocytes which produce antibodies of the subclass E (IgE) directed against the particular allergen. The interaction of specific IgE antibodies on the surface of effector cells (mast cells and basophils) with an allergen triggers the early phase of immediate type hypersensitivity responses.

Upon a second exposure to an allergen, IgE antibodies on mast cells recognize the allergen and bind to the invader. Granules in the mast cells then release pro-inflammatory substances such as histamine, platelet-activating factor, prostaglandins, cytokines and leukotrienes that trigger the allergy attack. Histamine stimulates mucus production and causes redness, swelling, and inflammation. Prostaglandins constrict airways and enlarge blood vessels.

Allergic rhinitis, or hay fever, is caused by allergic reactions of the mucous membranes in the nose and airway to allergens in the air. Symptoms of allergic rhinitis often include itchy nose, throat and eyes and excessive sneezing. Stuffy or runny nose often follow.

Rhinitis in the nasal passages can lead to asthma, which is a much more serious illness that occurs in the lungs. Asthma is characterized by development of airway hyperreactivity, breathlessness, wheezing on exhale, dry cough and a feeling of tightness in the chest. Repeated allergen exposure can sustain the inflammatory immune response in the airways, resulting in a remodeling of the airways, commonly known as chronic asthma. If the nasal inflammation reaches the sinuses, the result can be sinusitis, or rhino-sinusitis, in which the sinuses cannot empty themselves of bacteria. Symptoms include nasal congestion, runny nose, sore throat, fever, headache, fatigue and cough, as well as pain in the forehead, behind the cheeks, and even aching teeth and jaw.

The term "CB2 cannabinoid receptor (cannabinoid receptor 2 (macrophage), CB2, CNR2)" as used herein refers to is a G protein-coupled receptor encoded by the CNR2 gene. It is closely related to the CB receptor 1 that is responsible for the psychoactive properties of tetrahydrocannabinol. CB2 receptors are coupled to the MAPK/ERK pathway. The synthetic ligand CP-55,940 has been shown to preferentially inhibit adenylyl cyclase in CB2 receptors. The human CB1 and the CB2 receptors share approximately 44% amino acid similarity. When only the transmembrane regions of the receptors are considered, the amino acid similarly between the two receptor subtypes is approximately 68%. The amino acid sequence of the CB2 receptor is less highly conserved across human and rodent species as compared to the amino acid sequence of the CB1 receptor. Based on computer modeling, ligand interactions with CB2 receptor residues S3.31 and F5.46 appears to determine differences in CB1 versus CB2 receptor selectivity.

CB2 receptor mRNA has been found throughout the immune tissues of the spleen, tonsils and thymus gland, monocytes, macrophages, B-cells, and T-cells. CB2 receptor gene transcripts are also widely distributed throughout the brain, primarily on microglia (the immune cells of the CNS) but not neurons. CB2 receptors are also found throughout the gastrointestinal system, where they modulate intestinal inflammatory response. Thus, CB2 receptor agonists are a potential therapeutic target for inflammatory bowel diseases, such as Crohn's disease and ulcerative colitis.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "effective amount", "therapeutically-effective amount", and "therapeutically effective dose" as used herein means that amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated, or a reduction in a side-effect due to an administered pharmaceutical agent.

The term "IgE" as used herein refers to an immunoglobulin antibody of subclass E consisting consists of two identical heavy chains and two identical light chains held together by disulfide bonds in a "Y" shape-configuration. Each light chain consists of a variable domain linked to a constant domain, and each heavy chain consists of a variable domain and four constant domains. The two arms of an IgE antibody contain the site at which an IgE antibody binds to its specific antigen (allergen) and each arm is referred to as a Fab (fragment-antigen-binding) fragment. The tail of an IgE antibody is termed Fc. The Fc fragment of an IgE antibody consists of the constant domains and contains the biologically active structures of the IgE antibody (e.g., receptor binding sites).

The production of IgE antibodies requires interactions and collaborations among three cells; antigen presenting cells (APC), T lymphocytes (T helper cells; Th) and antibody-producing cells (B lymphocytes; B cells). When an allergen is introduced for the first time into a subject by such as inhalation of an environmental allergen, ingestion of certain foods, or via the skin, the allergen is taken up by APCs (e.g., macrophages) which then digest or process the allergen into smaller fragments (epitopes). These fragments are displayed on the surface of APCs in association with major histocompatibility complex proteins (MHC).

The allergen fragment/MHC complex on the surface of APCs is recognized and bound by receptors on the surface of specific T lymphocytes. This binding event leads to the activation of T lymphocytes and the subsequent expression and secretion of cytokines such as interleukin-4 (IL-4) that induce the multiplication, clonal expansion and differentiation of B cells specific for the allergen in question (B-cells that express on their surface immunoglobulin receptors capable of binding to the allergen) and ultimately lead to the production of IgE antibodies from these B cells. A portion of the activated T lymphocytes and IgE producing B cells eventually become committed to a pool of cells called T and B memory cells, which are capable of faster recognition of allergen upon subsequent exposure to the allergen.

Exposure to an allergen for a second time leads to the production of high levels of IgE antibodies specific for the allergen as a result of the involvement of memory B and T cells. The IgE antibodies lead to cross-linking of IgE receptors on mast cells and basophils by allergen-bound IgE, which in turn leads to the activation of these cells and the release of the pharmacological mediators responsible for the clinical manifestations of type I allergic diseases.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein refers to a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" as used herein refers to, but is not limited to, the acid addition salts of compounds of the present disclosure which are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine). Examples of such salts include, but are not limited to, benzoate, bicarbonate, sodium, calcium, acetate, laurate, malate, maleate, succinate, tannate, tartrate, benzenesulfonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrobromide, hydrochloride, hydroxynapthoate, iodide, isothionate, lactate, lactobionate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, stearate, subacetate, teoclate, tosylate, and valerate.

The term "organism" or "subject" refers to mammals, and especially humans, in need of treatment.

The term 'unit dosage form' as used herein refers to physically discrete units suitable as unitary dosages for human patients and other mammals with each unit containing a predetermined quantity of active material calculated to produce the desired therapeutic effect in association with suitable pharmaceutical carriers or excipients. The compositions according to the present disclosure may be formulated in a unit dosage form. A single daily unit dose also may be divided into 2 or 3 unit doses that are taken at different times throughout the day, or as a controlled release form, so as to reduce adverse side-effects as much as possible.

Description

The present disclosure encompasses embodiments of methods for reducing the level of immunoglobulin E (IgE) in the serum of an animal or human subject by administering to the subject an effective dose or doses, or an accumulated effective dose, of a pharmaceutical composition that comprises an agonist of the CB2 cannabinoid receptor. The present disclosure further encompasses pharmaceutical compositions suitable for administering to an animal or human subject to provide an effective amount of an agonist of the CB2 cannabinoid receptor to reduce the level of IgE in the recipient subject.

During the development of adaptive immunity to *Legionella pneumophila* infection, $\Delta^9$-tetrahydrocannabinol (THC) treatment prior to *Legionella pneumophila* infection causes a shift from the protective Th1 (cell-mediated) to non-protective Th2 (humoral or antibody) response (Newton et al., (1994) *Infect. Immun.* 62: 4015-4020; Klein et al., (2000) *J. Immunol.* 164: 6461-6466) and it involved both CB1 and CB2 cannabinoid receptors (Klein et al., (2000) *J. Immunol.* 164: 6461-6466; Newton et al., (2009) *J. Neuroimmune Pharmacol.* 4: 92-102). CB1 receptors are found in abundance in discrete areas of the brain and are responsible for the psychoactive effect of marijuana (Pertwee R G (1997) *Pharmacol. Ther.* 74: 129-180). CB2 receptors are expressed mainly in cells of the immune system and are called peripheral receptors (Klein T W (2005) *Nat. Rev. Immunol.* 5: 400-

411). A third cannabinoid receptor, GPR55, has been proposed and when activated by THC or an andamide increases intracellular calcium distinct from $CB_1$ and $CB_2$ (Baker et al., (2006) *Trends Pharmacol. Sci.* 27: 1-4; Lauckner et al., (2008) *Proc. Natl. Acad. Sci. U.S.A.* 105: 2699-2704). Lysophosphatidylinositol (LPI) is ligand for GPR55 but not $CB_1$ or $CB_2$ (Oka et al., (2007) *Biochem. Biophys. Res. Commun.* 362: 928-934).

In in vivo IgE-induction models using OVA/Alum or KLH/Ribi, the role of GPR55, in cannabinoid effects on antibody production has been investigated. BALB/c (B/c), C57BL/6 (B6), or B6 CB2 deficient ($CB2^{-/-}$) mice were pretreated with THC or L-α-lysophosphatidylinositol (LPI) prior to injections with OVA/Alum or KLH/Ribi, followed by boosting with same antigens. The mice were then bled on various days after boosting and total serum IgE was determined.

The IgE levels were elevated in THC-treated B/c mice in response to either OVA/Alum or KLH/Ribi. With OVA/ALUM, $CB2^{-/-}$ mice had increased levels of IgE over wild-type (B6) mice and pretreatment with THC augmented this effect. In line with this, treatment of mice with the highly selective CB2 agonist, Gp1a (N-(Piperidin-1-yl)-1-(2,4-dichlorophenyl)-1,4-dihydro-6-methylindeno[1,2-c]pyrazole-3-carboxamide), caused a decrease in IgE.

CB1 antagonist treatment of B6 and $CB2^{-/-}$ mice prior to THC dosing only slightly elevated the IgE response, suggesting that neither CB1 nor CB2 were involved in the IgE response. With KLH/RIBI, THC treatment increased IgE levels greater than OVA/ALUM; however, there were no differences between B6 and $CB2^{-/-}$ or THC/B6 and THC/$CB2^{-/-}$ mice. Pretreatment with the GPR55-selective agonist LPI enhanced IgE levels in B/c mice given OVA/ALUM. These studies suggest that GPR55 is involved in enhancing IgE production following treatment with THC and LPI, and that CB2 receptors have a suppressive role in the control of IgE.

In in vitro antibody-forming cell (AFC) studies, splenic B cells with CD40L stimulated from $CB1^{-/-}$/$CB2^{-/-}$ mice, as compared to C57BL/6 mice, have increased levels of IgM in the supernatant when treated with THC, implying that in the absence of CB1/CB2 there is elevated of IgM (Springs et al., (2008) *J. Leukoc. Biol.* 84: 1574-1584). In a further report of using OVA without adjuvant, anti-OVA IgE titers were higher, but not significantly, at 6 hr. Isolations of mRNA from lungs of these mice showed that there were increases in IL-4 and decreases in IFN-γ levels (Kaplan et al., (2010) *Toxicol. Pathol.* 38: 382-392.).

The CB2 receptor is involved with IgE-mediated triphasic cutaneous ear swelling (Ueda et al., (2007) *Life Sci.* 80: 414-419). This was based on CB2 deficient mice ($CB2^{-/-}$) failing to induce the ear swelling as well as an antagonist of CB2 (SR144528) attenuating these responses. Additionally, epicutaneous treatment with an analogue of 2-arachidonylglycerol, a ligand for CB2, induced the triphasic cutaneous ear swelling.

It has now been discovered that exposure of mammalian cells to compounds agonistic of the CB2 receptor are able to suppress the level of IgE antibodies in the sera of such treated subjects, thereby providing a method for modulating this type of antibody and reducing or eliminating a causative agent of allergic reactions. It has also been shown that the suppressive action of this agonist compound can be inhibited by a CB2 receptor antagonist compound, providing evidence that the agonist is acting through CB2 receptors. Also consistent with the observations on the IgE suppressive effects of CB2 receptor agonists, it has also been found that CB2-deficient mice (homozygous $CB2^{-/-}$) that do not express the CB2 gene have elevated serum levels of IgE, indicating that it is the activation of this receptor that is instrumental in reducing the formation or release into the serum of IgE antibodies.

The present disclosure, accordingly, also provides embodiments of a pharmaceutical composition that is formulated for the delivery of an effective therapeutic dose of a CB2 agonist to the peripheral cell CB2 receptors of an animal or human subject, thereby reducing IgE formation or secretion by the subject. It is also contemplated that the pharmaceutical compositions of the disclosure may be formulated to have less than a single effective dose, and that the effective dose may be accumulated in the recipient individual by administration to the recipient of multiple sub-optimal dosages.

Such pharmaceutical compositions can be advantageous for the relief of, for example, the symptoms of an allergic reaction mediated by IgE antibodies. The pharmaceutical compositions of the disclosure, therefore, comprise at least one agonist of the CB2 receptor such as agonists described by Mussinu et al., (2003) *Bioorganic Medicinal Chem.* 11: 251-263 and Merineddu et al., (2006) *J. Med. Chem.* 49: 7502-7512, both of which are incorporated herein by reference in their entireties. Such agonists, for example, may be selected from, but are not limited to, agonists of the following group, the structures of which are illustrated in FIGS. 1A-3: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-fluoro-N-piperidin-1-yl-1,4-dihydroindeno[1,2-c]pyrazole-3-carboxamide (1b); 6-Bromo-1-(2',4'-Dichlorophenyl)-N-piperidin-1-yl-1,4-dihydroindeno[1,2-c]pyrazole-3-carboxamide (1c); 1-(2',4'-Dichlorophenyl)-6-iodo-N-piperidin-1-yl-1,4-dihydroindeno[1,2-c]pyrazole-3-carboxamide (1d); 5-Chloro-1-(2',4'-Dichlorophenyl)-N-piperidin-1-yl-1,4-dihydroindeno[1,2-c]pyrazole-3-carboxamide (1e); 7-Chloro-1-(2',4'-Dichlorophenyl)-N-piperidin-1-yl-1,4-dihydroindeno[1,2-c]pyrazole-3-carboxamide (1f); 1-(2',4'-Dichlorophenyl)-N-piperidin-1-yl-1,4-dihydroindeno[1,2-c]pyrazole-3-carboxamide (1g); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methoxy-N-piperidin-1-yl-1,4-dihydroindeno[1,2-c]pyrazole-3-carboxamide (1i); 6-Chloro-1-(4'-chlorophenyl)-N-piperidin-1-yl-1,4-dihydroindeno[1,2-c]pyrazole-3-carboxamide (1j); 6-Chloro-1-phenyl-N-piperidin-1-yl-1,4-dihydroindeno[1,2-c]pyrazole-3-carboxamide (1k); 6-Chloro-1-(4'-chlorophenyl)-N-piperidin-1-yl-1,4-dihydroindeno[1,2-c]pyrazole-3-carboxamide (1l); 6-Chloro-1-(2',4'-Dichlorophenyl)-N-pyrrolidin-1-yl-1,4-dihydroindeno[1,2-c]pyrazole-3-carboxamide (1m); 6-Chloro-1-(2',4'-Dichlorophenyl)-N',N'-dimethyl-1,4-dihydroindeno[1,2-c]pyrazole-3-carbohydrazide (1n); 6-Chloro-1-(2',4'-Dichlorophenyl)-1,4-dihydroindeno[1,2-c]pyrazole-3-carbohydrazide (1o); 6-Chloro-1-(2',4'-Dichlorophenyl)-N-(4-methylpiperazin-1-yl)-1,4-dihydroindeno[1,2-c]pyrazole-3-carboxamide (1q); 6-Chloro-1-(2',4'-Dichlorophenyl)-N-[(1-ethylpyrrolidin-2-yl)methyl]-1,4-dihydroindeno[1,2-c]pyrazole-3-carboxamide (1r); 6-Chloro-1-(2',4'-Dichlorophenyl)-N'-(1-methylethylidene)-1,4-dihydroindeno[1,2-c]pyrazole-3-carbohydrazide (1p); 1-(2',4'-Dichlorophenyl)-6-methyl-N-cyclohexylamine-1,4-dihydroindeno[1,2-c]pyrazole-3-carboxamide (2a); 1-(2',4'-Dichlorophenyl)-6-methyl-N-phenyl-1,4-dihydroindeno-[1,2-c]pyrazole-3-carboxamide (2b); 1-(2',4'-Dichlorophenyl)-6-methyl-N-p-chlorophenyl-1,4-dihydroindeno[1,2-c]pyrazole-3-carboxamide (2c); 1-(2',4'-Dichlorophenyl)-6-methyl-N-p-fluorophenyl-1,4-dihydroindeno[1,2-c]pyrazole-3-carboxamide (2d); 1-(2',4'-Dichlorophenyl)-6-methyl-N-p-methylphenyl-1,4-dihydroindeno[1,2-c]pyrazole-3-carboxamide (2e); 1-(2',4'-

Dichlorophenyl)-6-methyl-N-p-methoxyphenyl-1,4-dihydroindeno[1,2-c]pyrazole-3-carboxamide (2g); 1-(2',4'-Dichlorophenyl)-6-methyl-N-phenyl-1,4-dihydroindeno-[1,2-c]pyrazole-3-carbohydrazide (2j); 1-(2',4'-Dichlorophenyl)-6-methyl-N-p-chlorophenyl-1,4-dihydroindeno[1,2-c]pyrazole-3-carbohydrazide (2k); 7-Chloro-1-(2',4'-Dichlorophenyl)-6-methyl-N-cyclohexylamine-1,4-dihydroindeno[1,2-c]pyrazole-3-carboxamide (2n); 7-Chloro-1-(2',4'-Dichlorophenyl)-6-methyl-N-piperidin-1-yl-1,4-dihydroindeno[1,2-c]pyrazole-3-carboxamide (2o); 6-Chloro-1-(2',4'-Dichlorophenyl)-7-methyl-N-piperidin-1-yl-1,4-dihydroindeno[1,2-c]pyrazole-3-carboxamide (2p); JWH133: 6aR,10aR)-3-(1,1-Dimethylbutyl)-6a,7,10,10a-tetrahydro-6,6,9-trimethyl-6H-dibenzo[b,d]pyran; JWH015: (2-Methyl-1-propyl-1H-indol-3-yl)-1-naphthalenylmethanone; HU308: [(1R,2R,5R)-2-[2,6-dimethoxy-4-(2-methyloctan-2-yl)phenyl]-7,7-dimethyl-4-bicyclo[3.1.1]hept-3-enyl]methanol; AM1241: (1-(methylpiperidin-2-ylmethyl)-3-(2-iodo-5-nitrobenzoyl)indole); and GW405833: 1-(2,3-Dichlorobenzoyl)-5-methoxy-2-methyl-3-[2-(4-morpholinyl)ethyl]-1H-indole. A particularly advantageous agonist, but not limiting, is Gpa1a (N-(Piperidin-1-yl)-1-(2,4-dichlorophenyl)-1,4-dihydro-6-methylindeno[1,2-c]pyrazole-3-carboxamide) (alternatively designated herein as compound (1h) 1-(2',4'-Dichlorophenyl)-6-methyl-N-piperidin-1-yl-1,4-dihydroindeno[1,2-c]pyrazole-3-carboxamide)

To the extent that the disclosed compounds, and salts thereof, may exist in their tautomeric form, all such tautomeric forms are contemplated herein as part of the present disclosure. All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974

The method of reducing the level of IgE in an animal or human subject described in the present disclosure may be carried out using a pharmaceutical composition comprising any of the compounds as defined herein and a pharmaceutically acceptable diluent, excipient, or carrier that can vary depending on the format of the unit dosage form and consistent with prior art and conventional pharmaceutical practices. In water, a carrier such as lecithin and/or oil such as rice bran or olive oil may be added to the composition to increase bioavailability of lipid-soluble agents.

The pharmaceutical composition may contain between about 0.01 mg and 5000 mg, between about 50 to about 2000 mg, or between 50 to about 1000 mg, of the compound, and may be formulated into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions.

To prepare the pharmaceutical compositions of this invention, one or more compounds of the present invention as the active ingredient can be intimately admixed with a pharmaceutical carrier according to conventional pharmaceutical compounding techniques, which carrier may take a wide variety of forms depending of the form of preparation desired for administration, e.g., oral. In preparing the compositions in oral dosage form, any of the usual pharmaceutical media may be employed.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

The liquid forms in which the novel compositions of the present invention may be incorporated for administration orally include the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous-suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate. For parenterals, the carrier will usually comprise sterile water, through other ingredients, for example, for purposes such as aiding solubility or for preservation, may be included.

The pharmaceutical compositions herein may contain, but are not necessarily limited to, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

An appropriate dosage level can be generally about 0.01 to 5000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

One aspect of the present application, therefore, encompasses embodiments of a method of reducing the level of immunoglobulin E (IgE) of an animal or human subject, the method comprising: administering to an animal or human subject an effective dose of a pharmaceutical composition comprising an agonist of a CB2 cannabinoid receptor, thereby reducing the level of IgE in the serum of the recipient subject.

In embodiments of this aspect of the disclosure, the pharmaceutical composition can further comprise a pharmaceutically acceptable carrier.

In embodiments of this aspect of the disclosure, the agonist of the CB2 cannabinoid receptor can be selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-fluoro-N-piperidin-1-yl-1,4-dihydroindeno[1,2-c]pyrazole-3-carboxamide (1b); 6-Bromo-1-(2',4'-Dichlorophenyl)-N-piperidin-1-yl-1, 4-dihydroindeno[1,2-c]pyrazole-3-carboxamide (1c); 1-(2',4'-Dichlorophenyl)-6-iodo-N-piperidin-1-yl-1,4-dihydroindeno[1,2-c]pyrazole-3-carboxamide (1d); 5-Chloro-1-(2',4'-Dichlorophenyl)-N-piperidin-1-yl-1,4-dihydroindeno[1,2-c]pyrazole-3-carboxamide (1e); 7-Chloro-1-(2',4'-Dichlorophenyl)-N-piperidin-1-yl-1,4-dihydroindeno[1,2-c]

pyrazole-3-carboxamide (1f); 1-(2',4'-Dichlorophenyl)-N-piperidin-1-yl-1,4-dihydroindeno[1,2-c]pyrazole-3-carboxamide (1g); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methoxy-N-piperidin-1-yl-1,4-dihydroindeno[1,2-c]pyrazole-3-carboxamide (1i); 6-Chloro-1-(4'-chlorophenyl)-N-piperidin-1-yl-1,4-dihydroindeno[1,2-c]pyrazole-3-carboxamide (1j); 6-Chloro-1-phenyl-N-piperidin-1-yl-1,4-dihydroindeno[1,2-c]pyrazole-3-carboxamide (1k); 6-Chloro-1-(4'-chlorophenyl)-N-piperidin-1-yl-1,4-dihydroindeno[1,2-c]pyrazole-3-carboxamide (1l); 6-Chloro-1-(2',4'-Dichlorophenyl)-N-pyrrolidin-1-yl-1,4-dihydroindeno[1,2-c]pyrazole-3-carboxamide (1m); 6-Chloro-1-(2',4'-Dichlorophenyl)-N',N'-dimethyl-1,4-dihydroindeno[1,2-c]pyrazole-3-carbohydrazide (1n); 6-Chloro-1-(2',4'-Dichlorophenyl)-1,4-dihydroindeno[1,2-c]pyrazole-3-carbohydrazide (1o); 6-Chloro-1-(2',4'-Dichlorophenyl)-N-(4-methylpiperazin-1-yl)-1,4-dihydroindeno[1,2-c]pyrazole-3-carboxamide (1q); 6-Chloro-1-(2',4'-Dichlorophenyl)-N-[(1-ethylpyrrolidin-2-yl)methyl]-1,4-dihydroindeno[1,2-c]pyrazole-3-carboxamide (1r); 6-Chloro-1-(2',4'-Dichlorophenyl)-N'-(1-methylethylidene)-1,4-dihydroindeno[1,2-c]pyrazole-3-carbohydrazide (1p); 1-(2',4'-Dichlorophenyl)-6-methyl-N-cyclohexylamine-1,4-dihydroindeno[1,2-c]pyrazole-3-carboxamide (2a); 1-(2',4'-Dichlorophenyl)-6-methyl-N-phenyl-1,4-dihydroindeno-[1,2-c]pyrazole-3-carboxamide (2b); 1-(2',4'-Dichlorophenyl)-6-methyl-N-p-chlorophenyl-1,4-dihydroindeno[1,2-c]pyrazole-3-carboxamide (2c); 1-(2',4'-Dichlorophenyl)-6-methyl-N-p-fluorophenyl-1,4-dihydroindeno[1,2-c]pyrazole-3-carboxamide (2d); 1-(2',4'-Dichlorophenyl)-6-methyl-N-p-methylphenyl-1,4-dihydroindeno[1,2-c]pyrazole-3-carboxamide (2e); 1-(2',4'-Dichlorophenyl)-6-methyl-N-p-methoxyphenyl-1,4-dihydroindeno[1,2-c]pyrazole-3-carboxamide (2g); 1-(2',4'-Dichlorophenyl)-6-methyl-N-phenyl-1,4-dihydroindeno-[1,2-c]pyrazole-3-carbohydrazide (2j); 1-(2',4'-Dichlorophenyl)-6-methyl-N-p-chlorophenyl-1,4-dihydroindeno[1,2-c]pyrazole-3-carbohydrazide (2k); 7-Chloro-1-(2',4'-Dichlorophenyl)-6-methyl-N-cyclohexylamine-1,4-dihydroindeno[1,2-c]pyrazole-3-carboxamide (2n); 7-Chloro-1-(2',4'-Dichlorophenyl)-6-methyl-N-piperidin-1-yl-1,4-dihydroindeno[1,2-c]pyrazole-3-carboxamide (2o); 6-Chloro-1-(2',4'-Dichlorophenyl)-7-methyl-N-piperidin-1-yl-1,4-dihydroindeno[1,2-c]pyrazole-3-carboxamide (2p); JWH133: 6aR,10aR)-3-(1,1-Dimethylbutyl)-6a,7,10,10a-tetrahydro-6,6,9-trimethyl-6H-dibenzo[b,d]pyran; JWH015: (2-Methyl-1-propyl-1H-indol-3-yl)-1-naphthalenylmethanone; HU308: [(1R,2R,5R)-2-[2,6-dimethoxy-4-(2-methyloctan-2-yl)phenyl]-7,7-dimethyl-4-bicyclo[3.1.1]hept-3-enyl]methanol; AM1241: (1-(methylpiperidin-2-ylmethyl)-3-(2-iodo-5-nitrobenzoyl)indole); and GW405833: 1-(2,3-Dichlorobenzoyl)-5-methoxy-2-methyl-3-[2-(4-morpholinyl)ethyl]-1H-indole.

In some embodiments of this aspect of the disclosure, the agonist of the CB2 cannabinoid receptor can be selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methyl-N-cyclohexylamine-1,4-dihydroindeno[1,2-c]pyrazole-3-carboxamide (2a); and 1-(2',4'-Dichlorophenyl)-6-methyl-N-phenyl-1,4-dihydroindeno-[1,2-c]pyrazole-3-carboxamide (2b).

In some embodiments of this aspect of the disclosure, the agonist of the CB2 cannabinoid receptor can be 1-(2',4'-Dichlorophenyl)-6-methyl-N-piperidin-1-yl-1,4-dihydroindeno[1,2-c]pyrazole-3-carboxamide (1h) (alternatively designated Gp1a).

Another aspect of the disclosure encompasses embodiments of pharmaceutical composition comprising an effective dose of an agonist of a CB2 cannabinoid receptor and a pharmaceutically acceptable carrier, wherein the pharmaceutical composition is formulated to reducing the level of IgE in the serum of the subject animal or human when administered thereto.

In embodiments of this aspect of the disclosure the agonist of the CB2 cannabinoid receptor can be selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-fluoro-N-piperidin-1-yl-1,4-dihydroindeno[1,2-c]pyrazole-3-carboxamide (1b); 6-Bromo-1-(2',4'-Dichlorophenyl)-N-piperidin-1-yl-1,4-dihydroindeno[1,2-c]pyrazole-3-carboxamide (1c); 1-(2',4'-Dichlorophenyl)-6-iodo-N-piperidin-1-yl-1,4-dihydroindeno[1,2-c]pyrazole-3-carboxamide (1d); 5-Chloro-1-(2',4'-Dichlorophenyl)-N-piperidin-1-yl-1,4-dihydroindeno[1,2-c]pyrazole-3-carboxamide (1e); 7-Chloro-1-(2',4'-Dichlorophenyl)-N-piperidin-1-yl-1,4-dihydroindeno[1,2-c]pyrazole-3-carboxamide (1f); 1-(2',4'-Dichlorophenyl)-N-piperidin-1-yl-1,4-dihydroindeno[1,2-c]pyrazole-3-carboxamide (1g); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methoxy-N-piperidin-1-yl-1,4-dihydroindeno[1,2-c]pyrazole-3-carboxamide (1i); 6-Chloro-1-(4'-chlorophenyl)-N-piperidin-1-yl-1,4-dihydroindeno[1,2-c]pyrazole-3-carboxamide (1j); 6-Chloro-1-phenyl-N-piperidin-1-yl-1,4-dihydroindeno[1,2-c]pyrazole-3-carboxamide (1k); 6-Chloro-1-(4'-chlorophenyl)-N-piperidin-1-yl-1,4-dihydroindeno[1,2-c]pyrazole-3-carboxamide (1l); 6-Chloro-1-(2',4'-Dichlorophenyl)-N-pyrrolidin-1-yl-1,4-dihydroindeno[1,2-c]pyrazole-3-carboxamide (1m); 6-Chloro-1-(2',4'-Dichlorophenyl)-N',N'-dimethyl-1,4-dihydroindeno[1,2-c]pyrazole-3-carbohydrazide (1n); 6-Chloro-1-(2',4'-Dichlorophenyl)-1,4-dihydroindeno[1,2-c]pyrazole-3-carbohydrazide (1o); 6-Chloro-1-(2',4'-Dichlorophenyl)-N-(4-methylpiperazin-1-yl)-1,4-dihydroindeno[1,2-c]pyrazole-3-carboxamide (1q); 6-Chloro-1-(2',4'-Dichlorophenyl)-N-[(1-ethylpyrrolidin-2-yl)methyl]-1,4-dihydroindeno[1,2-c]pyrazole-3-carboxamide (1r); 6-Chloro-1-(2',4'-Dichlorophenyl)-N'-(1-methylethylidene)-1,4-dihydroindeno[1,2-c]pyrazole-3-carbohydrazide (1p); 1-(2',4'-Dichlorophenyl)-6-methyl-N-cyclohexylamine-1,4-dihydroindeno[1,2-c]pyrazole-3-carboxamide (2a); 1-(2',4'-Dichlorophenyl)-6-methyl-N-phenyl-1,4-dihydroindeno-[1,2-c]pyrazole-3-carboxamide (2b); 1-(2',4'-Dichlorophenyl)-6-methyl-N-p-chlorophenyl-1,4-dihydroindeno[1,2-c]pyrazole-3-carboxamide (2c); 1-(2',4'-Dichlorophenyl)-6-methyl-N-p-fluorophenyl-1,4-dihydroindeno[1,2-c]pyrazole-3-carboxamide (2d); 1-(2',4'-Dichlorophenyl)-6-methyl-N-p-methylphenyl-1,4-dihydroindeno[1,2-c]pyrazole-3-carboxamide (2e); 1-(2',4'-Dichlorophenyl)-6-methyl-N-p-methoxyphenyl-1,4-dihydroindeno[1,2-c]pyrazole-3-carboxamide (2g); 1-(2',4'-Dichlorophenyl)-6-methyl-N-phenyl-1,4-dihydroindeno-[1,2-c]pyrazole-3-carbohydrazide (2j); 1-(2',4'-Dichlorophenyl)-6-methyl-N-p-chlorophenyl-1,4-dihydroindeno[1,2-c]pyrazole-3-carbohydrazide (2k); 7-Chloro-1-(2',4'-Dichlorophenyl)-6-methyl-N-cyclohexylamine-1,4-dihydroindeno[1,2-c]pyrazole-3-carboxamide (2n); 7-Chloro-1-(2',4'-Dichlorophenyl)-6-methyl-N-piperidin-1-yl-1,4-dihydroindeno[1,2-c]pyrazole-3-carboxamide (2o); and 6-Chloro-1-(2',4'-Dichlorophenyl)-7-methyl-N-piperidin-1-yl-1,4-dihydroindeno[1,2-c]pyrazole-3-carboxamide (2p), and a pharmaceutically acceptable carrier, and wherein the therapeutic dose is effective in reducing the level of immunoglobulin IgE in an animal or human subject in receipt of said pharmaceutical composition.

In some embodiments of this aspect of the disclosure, the agonist of the CB2 cannabinoid receptor is selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methyl-N-cyclohexylamine-1,4-dihydroindeno[1,2-c]pyrazole-3-carboxamide (2a); 1-(2',4'-Dichlorophenyl)-6-methyl-N-phenyl-1,4-dihydroindeno-[1,2-c]pyrazole-3-carboxamide (2b); JWH133: 6aR,10aR)-3-(1,1-Dimethylbutyl)-6a,7,10,10a-tetrahydro-6,6,9-trimethyl-6H-dibenzo[b,d]pyran; JWH015: (2-Methyl-1-propyl-1H-indol-3-yl)-1-naphthalenylmethanone; HU308: [(1R,2R,5R)-2-[2,6-dimethoxy-4-(2-methyloctan-2-yl)phenyl]-7,7-dimethyl-4-bicyclo[3.1.1]hept-3-enyl] methanol; AM1241: (1-(methylpiperidin-2-ylmethyl)-3-(2-iodo-5-nitrobenzoyl)indole); and GW405833: 1-(2,3-Dichlorobenzoyl)-5-methoxy-2-methyl-3-[2-(4-morpholinyl)ethyl]-1H-indole.

In some embodiments of this aspect of the disclosure, the agonist of the CB2 cannabinoid receptor is 1-(2',4'-Dichlorophenyl)-6-methyl-N-piperidin-1-yl-1,4-dihydroindeno[1,2-c]pyrazole-3-carboxamide (1h).

In some embodiments of this aspect of the disclosure, the composition can be formulated for the delivery of the CB2 cannabinoid agonist to an animal or human subject via a route selected from orally, subcutaneously, intraperitoneally, intravenously, transdermally, and nasally.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Figure 1B:
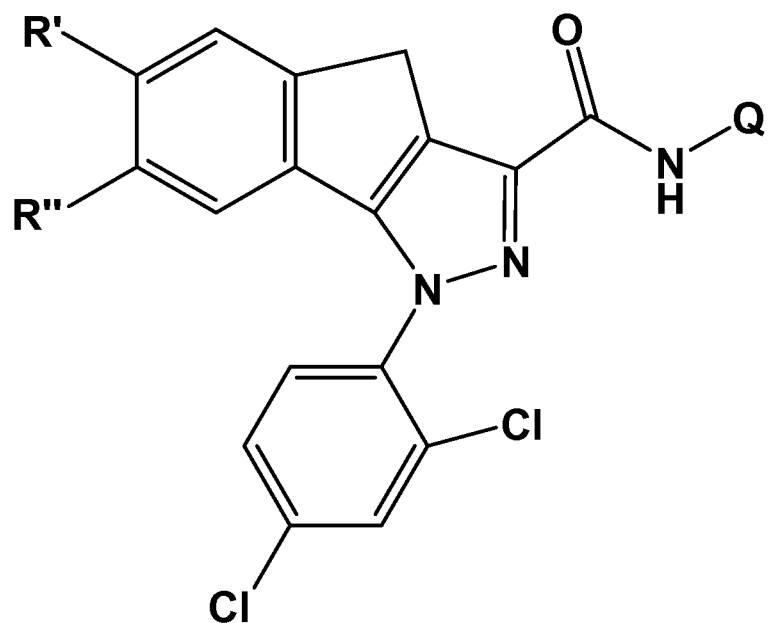
FIG. 1B illustrates the structure of formula 2, derivatives of which are illustrated in FIG. 3
Figure 2:
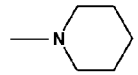
FIG. 2 illustrates derivative substituents of formula 1 shown in FIG. 1A.
Figure 2:
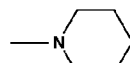
Figure 2:
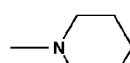
Figure 2:
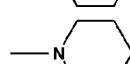
Figure 2:
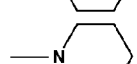
Figure 2:
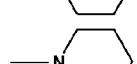
Figure 2:
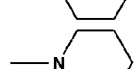
Figure 2:
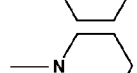
Figure 2:
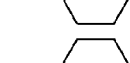
Figure 2:
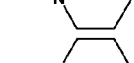
Figure 2:
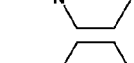
Figure 2:
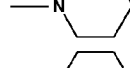
Figure 2:
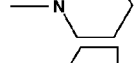
Figure 2:
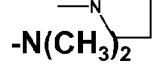
Figure 2:
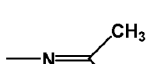
Figure 2:
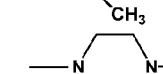
Figure 3:
FIG. 3 illustrates derivative substituents of formula 2 shown in FIG. 1B.
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:
Figure 3:
Figure 4:
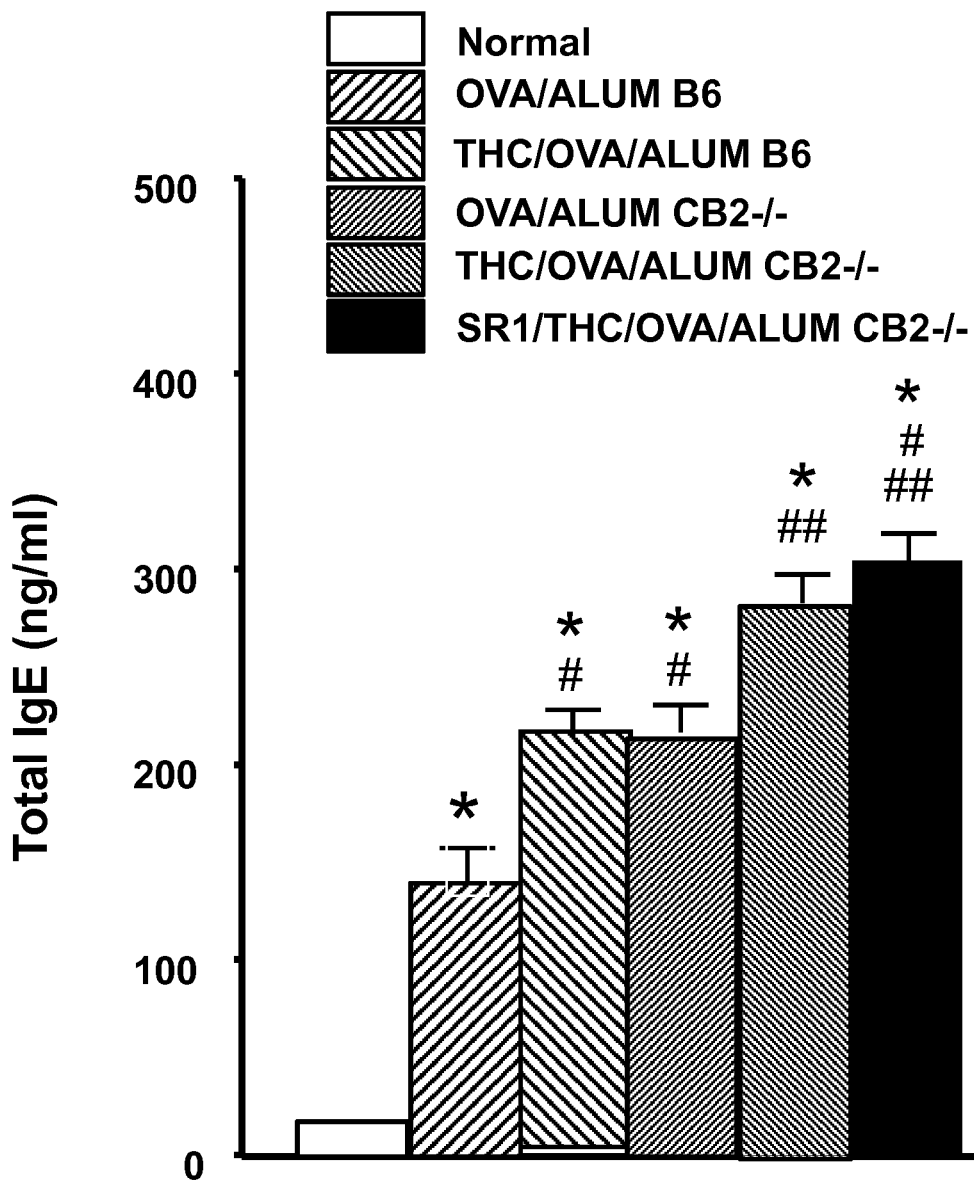
FIG. 4 is a graph illustrating that serum levels of total IgE were increased with THC pretreatment over C57BL/6 (B6) mice; CB2 deficient mice (CB2$^{-/-}$) over B6; and THC pretreatment CB2$^{-/-}$ over B6 and THC/B6. SR141716A (SR1.
Figure 5:
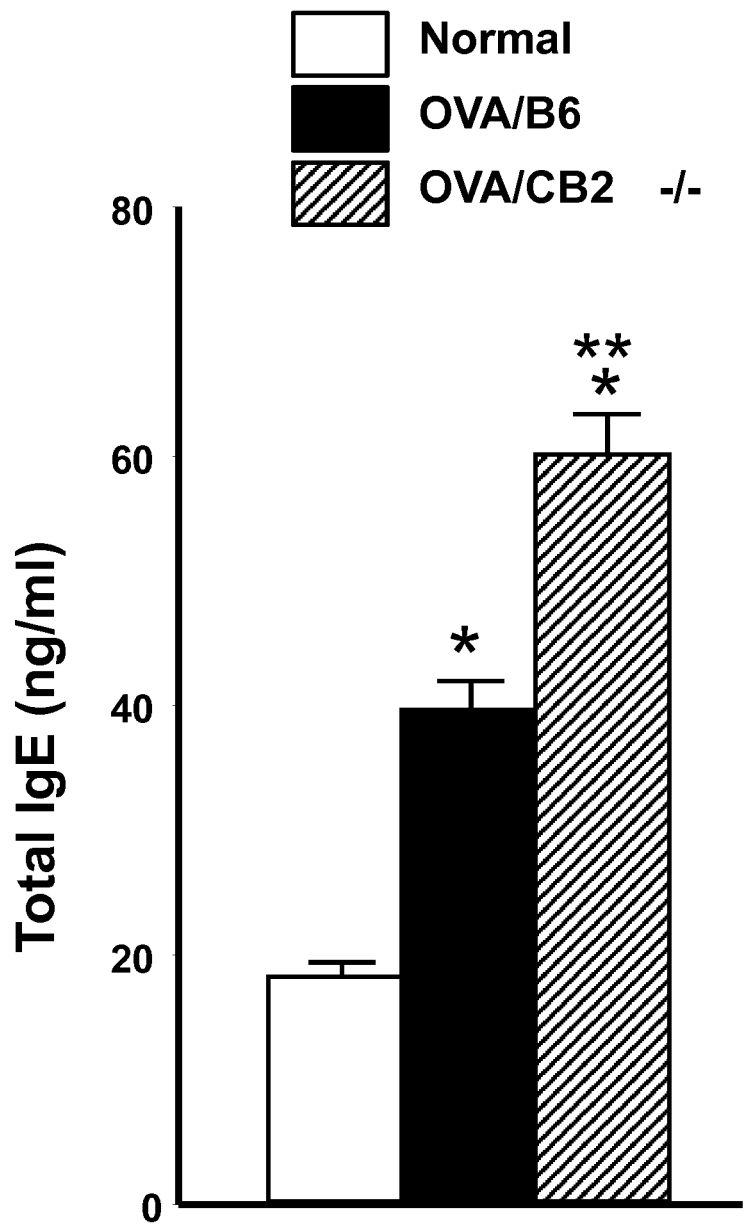
FIG. 5 is a graph illustrating that CB2-deficient (CB2$^{-/-}$) mice had elevated serum levels of total IgE over CB2-containing (CB2+/+) mice.
Figure 6:
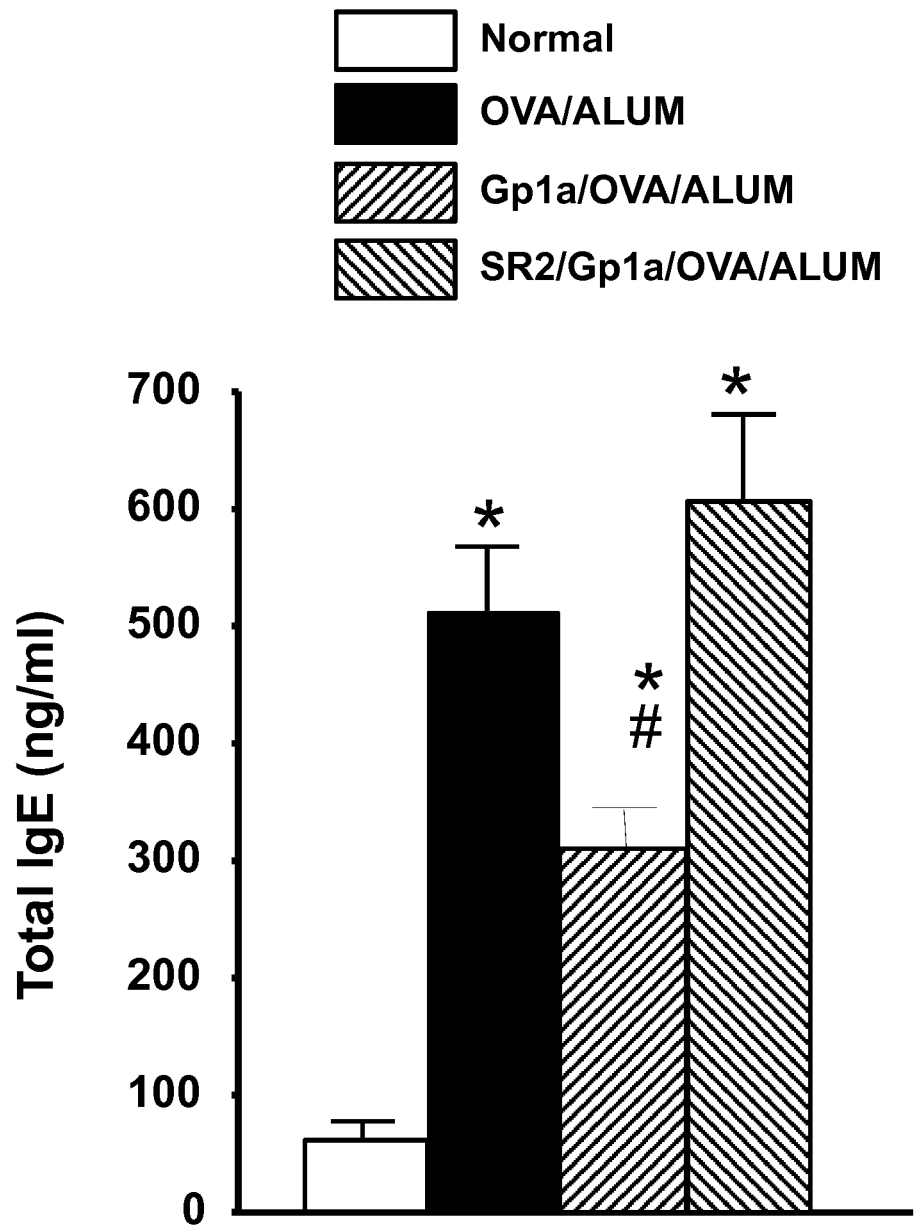
FIG. 6 is a graph illustrating that Gp1a, a CB2 agonist (Ki=0.0 37 nM), attenuates the serum levels of total IgE from BALB/c mice, and that co-treatment with the CB2 antagonist SR144528 reverses the Gp1a effect.

Mice deficient in $CB_2$ receptors ($CB_2$–/–) have increased serum levels of IgE antibodies. Mice were treated with ovalbumin/aluminum hydroxide-magnesium hydroxide (OVA/ALUM) following a boost of same antigen. The sera were collected at days 9-10 after the boost and ELISAs were performed. Data, as shown in FIG. 1, represented serum from individual mice (3-8 mice/group+/–SEM). *=$p \leq 0.05$ from normal; **=$p \leq 0.05$ from OVA/ALUM.

Example 2

Gp1a (N-(Piperidin-1-yl)-1-(2,4-dichlorophenyl)-1,4-dihydro-6-methylindeno[1,2-c]pyrazole-3-carboxamide) (Tocris Bioscience, Ellisville, Mo.), a $CB_2$ agonist (Ki=0.037 nM), attenuated the serum levels of total IgE in BALB/c mice and this Gp1a effect was reversed by SR144528 (5-(4-chloro-3-methylphenyl)-1-[(4-methylphenyl)methyl]-N-[(1S,2S,4R)-1,3,3-trimethylbicyclo[2.2.1]hept-2-yl]-1H-pyrazole-3-carboxamide) (Cayman Chemicals Co., Ann Arbor, Mich.) ($CB_2$ antagonist, SR2).

Mice were pretreated with SR2/Gp1a, Gp1a, or not pretreated, and 18 hrs later were sensitized with OVA/ALUM followed by a boost with same antigen. The sera were collected 6 days after the antigen boost injection and ELISAs were performed for IgE. Data represent sera from 4-8 mice/group+/–SEM. *=$p \leq 0.05$ from Normal; #=$p \leq 0.05$ from OVA/ALUM or SR2/OVA/ALUM.

We claim:

1. A method of reducing the level of immunoglobulin E (IgE) in the serum of an animal or human subject, the method comprising:
   administering to an animal or human subject an effective dose of a pharmaceutical composition comprising an agonist of a CB2 cannabinoid receptor, thereby reducing the level of IgE in the serum of the recipient subject.

2. The method of claim 1, wherein the pharmaceutical composition further comprises a pharmaceutically acceptable carrier.

3. The method of claim 1, wherein the agonist of the CB2 cannabinoid receptor is selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-fluoro-N-piperidin-1-yl-1,4-dihydroindeno[1,2-c]pyrazole-3-carboxamide (1 b); 6-Bromo-1-(2',4'-Dichlorophenyl)-N-piperidin-1-yl-1,4-dihydroindeno[1,2-c]pyrazole-3-carboxamide (1c); 1-(2',4'-Dichlorophenyl)-6-iodo-N-piperidin-1-yl-1,4-dihydroindeno[1,2-c]pyrazole-3-carboxamide (1d); 5-Chloro-1-(2',4'-Dichlorophenyl)-N-piperidin-1-yl-1,4-dihydroindeno[1,2-c]pyrazole-3-carboxamide (1e); 7-Chloro-1-(2',4'-Dichlorophenyl)-N-piperidin-1-yl-1,4-dihydroindeno[1,2-c]pyrazole-3-carboxamide (1f); 1-(2',4'-Dichlorophenyl)-N-piperidin-1-yl-1,4-dihydroindeno[1,2-c]pyrazole-3-carboxamide (1g); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methoxy-N-piperidin-1-yl-1,4-dihydroindeno[1,2-c]pyrazole-3-carboxamide (1i); 6-Chloro-1-(4-chlorophenyl)-N-piperidin-1-yl-1,4-dihydroindeno[1,2-c]pyrazole-3-carboxamide (1j); 6-Chloro-1-phenyl-N-piperidin-1-yl-1,4-dihydroindeno[1,2-c]pyrazole-3-carboxamide (1k); 6-Chloro-1-(4'-chlorophenyl)-N-piperidin-1-yl-1,4-dihydroindeno[1,2-c]pyrazole-3-carboxamide (1l); 6-Chloro-1-(2',4'-Dichlorophenyl)-N-pyrrolidin-1-yl-1,4-dihydroindeno[1,2-c]pyrazole-3-carboxamide (1m); 6-Chloro-1-(2',4'-Dichlorophenyl)-N',N'-dimethyl-1,4-dihydroindeno[1,2-c]pyrazole-3-carbohydrazide (1n); 6-Chloro-1-(2',4'-Dichlorophenyl)-1,4-dihydroindeno[1,2-c]pyrazole-3-carbohydrazide (1o); 6-Chloro-1-(2',4'-Dichlorophenyl)-N-(4-methylpiperazin-1- yl)-1,4-dihydroindeno[1,2-c]pyrazole-3-carboxamide (1q); 6-Chloro-1-(2',4'-Dichlorophenyl)-N-[(1-ethylpyrrolidin-2-yl)methyl]-1,4-dihydroindeno[1,2-c]pyrazole-3-carboxamide (1r); 6-Chloro-1-(2',4'-Dichlorophenyl)-N'-(1-methylethylidene)-1,4-dihydroindeno[1,2-c]pyrazole-3-carbohydrazide (1p); 1-(2',4'-Dichlorophenyl)-6-methyl-N-cyclohexylamine-1,4-dihydroindeno[1,2-c]pyrazole-3-carboxamide (2a); 1-(2',4'-Dichlorophenyl)-6-methyl-N-phenyl-1,4-dihydroindeno-[1,2-c]pyrazole-3-carboxamide (2b); 1-(2',4'-Dichlorophenyl)-6-methyl-N-p-chlorophenyl-1,4-dihydroindeno[1,2-c]pyrazole-3-carboxamide (2c); 1-(2',4'-Dichlorophenyl)-6-methyl-N-p-fluorophenyl-1,4-dihydroindeno[1,2-c]pyrazole-3-carboxamide (2d); 1-(2',4'-Dichlorophenyl)-6-methyl-N-p-methylphenyl-1,4-dihydroindeno[1,2-c]pyrazole-3-carboxamide (2e); 1-(2',4'-Dichlorophenyl)-6-methyl-N-p-methoxyphenyl-1,4-dihydroindeno[1,2-c]pyrazole-3-carboxamide (2g); 1-(2',4'-Dichlorophenyl)-6-methyl-N-phenyl-1,4-dihydroindeno-[1,2-c]pyrazole-3-carbohydrazide (2j); 1-(2',4'-Dichlorophenyl)-6-methyl-N-p-chlorophenyl-1,4-dihydroindeno[1,2-c]pyrazole-3-carbohydrazide (2k); 7-Chloro-1-(2',4'-Dichlorophenyl)-6-methyl-N-cyclohexylamine-1,4-dihydroindeno[1,2-c]pyrazole-3-carboxamide (2n); 7-Chloro-1-(2',4'-Dichlorophenyl)-6-methyl-N-piperidin-1-yl-1,4-dihydroindeno[1,2-c]pyrazole-3-carboxamide (2o); 6-Chloro-1-(2',4'-Dichlorophenyl)-7-methyl-N-piperidin-1-yl-1,4-dihydroindeno[1,2-c]pyrazole-3-carboxamide (2p); JWH133: 6aR,10aR)-3-(1,1-Dimethylbutyl)-6a,7,10,10a-tetrahydro-6,6,9-trimethyl-6H-dibenzo[b,d]pyran; JWH015: (2-Methyl-1-propyl-1H-indol-3-yl)-1-naphthalenylmethanone; HU308: [(1R,2R,5R)-2-[2,6-dimethoxy-4-(2-methyloctan-2-yl)phenyl]-7,7-dimethyl-4-bicyclo[3.1.1]hept-3-enyl]methanol; AM1241: (1-(methylpiperidin-2-ylmethyl)-3-(2-iodo-5-nitrobenzoyl)indole); and GW405833: 1-(2,3-Dichlorobenzoyl)-5-methoxy-2-methyl-3-[2-(4-morpholinyl)ethyl]-1H-indole.

4. The method of claim 3, wherein the agonist of the CB2 cannabinoid receptor is selected from the group consisting of: 6-Chloro-1-(2',4'-Dichlorophenyl)-N-piperidin-1-yl-1,4-dihydroindeno[1,2-c]pyrazole-3-carboxamide (1a); 1-(2',4'-Dichlorophenyl)-6-methyl-N-piperidin-1-yl-1,4-dihydroindeno[1,2-c]pyrazole-3-carboxamide (1h); 1-(2',4'-Dichlorophenyl)-6-methyl-N-cyclohexylamine-1,4-dihydroindeno[1,2-c]pyrazole-3-carboxamide (2a); and 1-(2',4'-Dichlorophenyl)-6-methyl-N-phenyl-1,4-dihydroindeno-[1,2-c]pyrazole-3-carboxamide (2b).

5. The method of claim 3, wherein the agonist of the CB2 cannabinoid receptor is 1-(2',4'-Dichlorophenyl)-6-methyl-N-piperidin-1-yl-1,4-dihydroindeno[1,2-c]pyrazole-3-carboxamide (1h).

* * * * *